(12) United States Patent
Kreindel

(10) Patent No.: US 7,238,183 B2
(45) Date of Patent: Jul. 3, 2007

(54) SYSTEM AND METHOD FOR TREATING SKIN

(75) Inventor: Michael Kreindel, Haifa (IL)

(73) Assignee: Syneron Medical Ltd., Yokneam Ellit (IL)

( * ) Notice: Subject to any disclaimer, the term of this patent is extended or adjusted under 35 U.S.C. 154(b) by 258 days.

(21) Appl. No.: 10/774,478

(22) Filed: Feb. 10, 2004

(65) Prior Publication Data

US 2004/0220512 A1    Nov. 4, 2004

Related U.S. Application Data

(63) Continuation-in-part of application No. 10/051,285, filed on Jan. 22, 2002, now abandoned.

(51) Int. Cl.
*A61B 18/18* (2006.01)
(52) U.S. Cl. .................. 606/41; 606/13; 607/101
(58) Field of Classification Search .............. 606/2, 606/3, 10–17, 32–34, 37–42, 48–50; 607/101–105
See application file for complete search history.

(56) References Cited

U.S. PATENT DOCUMENTS

| 5,509,916 | A | * | 4/1996 | Taylor | 606/13 |
| 5,755,753 | A | * | 5/1998 | Knowlton | 607/98 |
| 5,846,252 | A | | 12/1998 | Mehl, Sr. | |
| 5,948,011 | A | | 9/1999 | Knowlton | |
| 6,053,909 | A | * | 4/2000 | Shadduck | 606/3 |
| 6,139,569 | A | * | 10/2000 | Ingle et al. | 607/104 |
| 6,162,217 | A | | 12/2000 | Kannenberg et al. | |
| 6,306,160 | B1 | | 10/2001 | Nidetzky | |
| 6,413,255 | B1 | * | 7/2002 | Stern | 606/41 |
| 6,436,064 | B1 | | 8/2002 | Kloecker | |
| 6,436,094 | B1 | | 8/2002 | Reuter | |
| 2002/0128648 | A1 | | 9/2002 | Weber et al. | |

FOREIGN PATENT DOCUMENTS

| WO | WO 99/35983 | 7/1999 |
| WO | WO 00/53113 | 9/2000 |

* cited by examiner

*Primary Examiner*—Michael Peffley
(74) *Attorney, Agent, or Firm*—Browdy and Neimark, PLLC

(57) ABSTRACT

System and method for treating a skin target. A temperature effector creates a temperature difference between the target and the skin tissue surrounding the target such that the target is at a higher temperature than the surrounding tissue by at least 5° C. One or more RF electrodes are attached to the skin and RF energy is applied.

8 Claims, 3 Drawing Sheets

SYSTEM AND METHOD FOR TREATING SKIN

This application is a continuation-in-part of U.S. Ser. No. 10/051,285 filed Jan. 22, 2002, now abandoned.

FIELD OF THE INVENTION

This invention relates to methods and systems for treating skin.

BACKGROUND OF THE INVENTION

The term "target" is used herein to denote a skin defect such as a vascular lesion, pigmented lesion, acne, unwanted hair or wrinkle. Selective thermal treatment of skin is commonly used in aesthetic medicine to remove skin targets. In order to be destroyed, the target must be raised to a temperature of about 70° C. without raising the temperature of the surrounding epidermis or dermis to damaging levels. The most popular method of thermal skin treatment is selective photo-thermolysis in which light energy produced by a laser or flash lamp is selectively absorbed by a pigmented portion of the target. However, with this method it is often not possible to heat the entire target to a temperature necessary for destroying it without heating the surrounding skin to damaging levels. The main problem is that the optical contrast between the target and the surrounding skin tissue is not high enough to obtain a significant difference in temperature between the target and the surrounding skin tissue.

U.S. Pat. No. 5,755,753 discloses use of the radio-frequency (RF) range of electro-magnetic energy for skin tightening, where RF energy is applied to a pre-cooled skin surface. U.S. Pat. No. 5,846,252 discloses treating hairs to reduce their electrical resistance and then applying RF current.

SUMMARY OF THE INVENTION

The present invention is based upon the finding that selective heating of a skin target by RF energy is enhanced if prior to the application of the RF energy the skin is treated to make the temperature of the target ($T_t$) at least 5 centigrade degrees (5° C.) higher than the temperature of the surrounding skin tissue ($T_s$). The initial temperature gradient ($T_t-T_s>5°$ C.) between the target and surrounding tissue may be achieved either by pre-heating the target or pre-cooling the surrounding tissue.

The invention thus provides a system for treating a skin target comprising:
(a) one or more RF electrodes configured to be attached to the skin, so as to apply an RF current to the skin;
(b) a temperature effector configured to create a temperature gradient between the target and skin surrounding the target such that the target is at least 5 centigrade degrees warmer than the surrounding skin.

The invention still further provides a method for treating a skin target comprising:
a) creating a temperature gradient between the target and skin surrounding the target such that the target is at least 5 centigrade degrees warmer than the surrounding skin; and
b) applying RF energy to the skin.

The system and method of the invention may be used for such skin targets as a vascular lesion, pigmented lesion, hair follicle, wrinkle and acne.

While not wishing to be bound by a particular theory, it is believed that selective thermolysis of a target by RF energy is enhanced when $T_t-T_s>5°$ C., due to an increase in the electrical conductivity in the RF range of tissues when the tissue temperature is increased [Frances A. Duck, Physical Properties of Tissue, a Comprehensive Reference Book, Academic Press, 1990, p. 173]. Accordingly, the dependence of the conductivity σ of a tissue on temperature T is given by:

$$\sigma=\sigma_0(1+\alpha(T-T_0)) \quad (1)$$

where $\sigma_0$ is the conductivity at the reference temperature $T_0$ and α is a constant known as the temperature coefficient.

Heat generation by RF current can be estimated by Joule's Law:

$$H=\sigma E^2 \quad (2)$$

and the change in temperature in the tissue is obtained using the heat conductivity equation:

$$c\rho \frac{\partial T}{\partial t} = H \quad (3)$$

where c is the heat capacity of the tissue, ρ is the mass density and E is the intensity of the electric field.

Inserting Equations 1 and 2 into (3), $$c\rho \frac{\partial T}{\partial t} = \sigma_o(1+\alpha(T-T_o)E^2 \quad (4)$$

$$\text{Setting } A = \frac{\alpha \sigma_o E^2}{c\rho} \quad (5)$$

and integrating Equation 4, the result is $$T' = T_0 + \frac{e^{At}-1}{\alpha} + (T_i - T_o)e^{At} \quad (6)$$

where $T_i$ is the initial temperature of the tissue before the application of RF energy, t is the duration of the application of RF energy, and T' is the final temperature of the tissue at the end of the application of RF energy.

If the initial temperatures of the target and surrounding skin tissue are $T_t$ and $T_s$ respectively ($T_t-T_s>0$), then Equation 6 becomes for the target:

$$T'_t = T_0 + \frac{e^{At-1}}{\alpha} + (T_{ti} - T_{to})Ae^{it} \quad (7)$$

and for the surrounding skin, $$T'_s = T'_0 + \frac{e^{At}-1}{\alpha} + (T_{si} - T_o)e^{At} \quad (8)$$

subtracting Equation (8) from Equation (7) yields $$T_t'-T_s'=(T_{ti}-T_{si})e^{At} \quad (9)$$

where $T_{t_i}-T_{s_j}$ is the initial temperature gradient between the target and the surrounding skin, and $T_t'-T_s'$ is the final temperature gradient. Equation (9) shows that as the RF current is applied, the temperature gradient increases exponentially. Therefore, by creating an initial relatively small temperature gradient $Tt_i-Ts_i>5°$ C., and applying RF energy, a larger temperature gradient is obtained. This allows heating of the target to a sufficiently high temperature to destroy the target without heating the surrounding skin tissues to damaging levels.

Assuming a typical RF fluence (F) in the skin of $20 \text{ J/cm}^2$, $\alpha=0.03$ $(°\text{ C.})^{-1}$ and a heat capacitance $c\rho=3.6 \text{ J/cm}^3 \text{ °K}$, the factor $e^{At}$ in Equation (9) is $$e^{At} = e^{\frac{\alpha\sigma_o E^2}{c\rho}} = e^{\frac{\alpha Ht}{c\rho}} = e^{0.83} = 2.3$$

Thus, the temperature gradient increases by a factor of about 2.3 during the application of the RF energy.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF THE INVENTION

Figure 1:
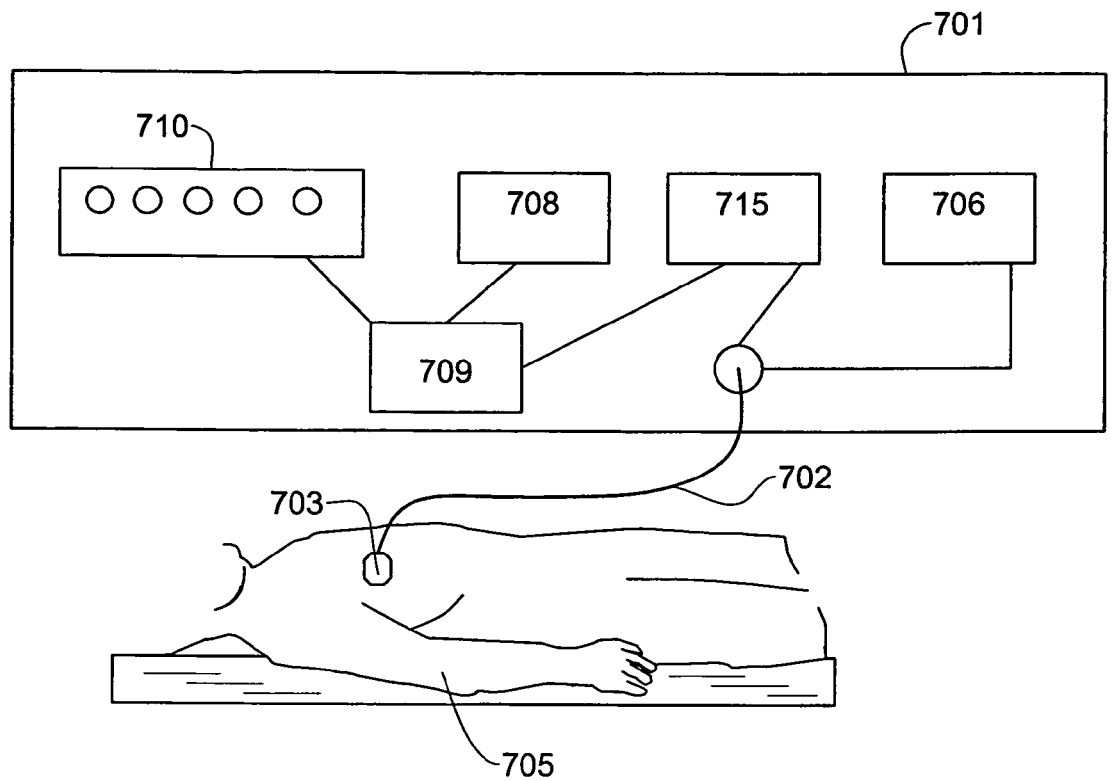
FIG. 1 shows a system for heating a skin target and applying RF to an individual in accordance with one embodiment of the invention.
Figure 2:
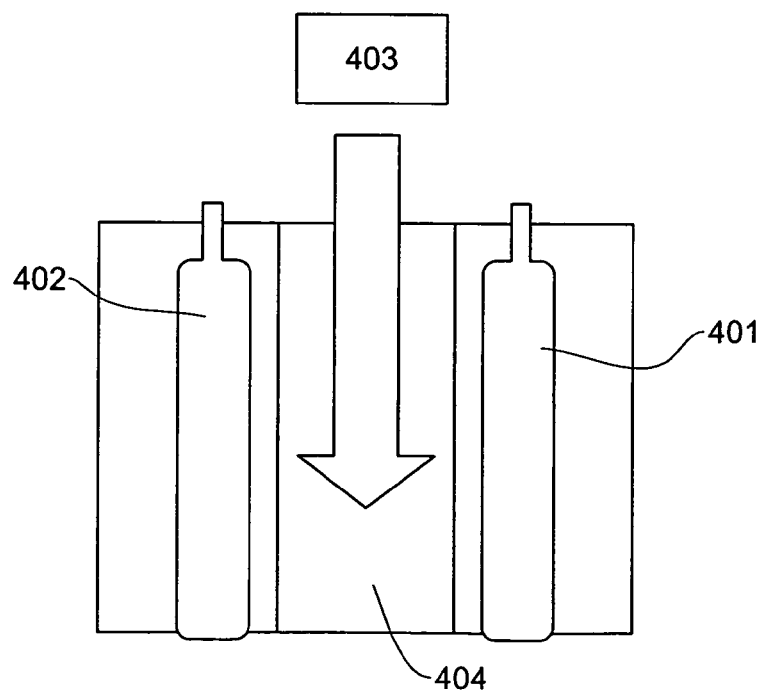
FIG. 2 shows a method for treating skin using the system of FIG. 1.

Referring to FIGS. 1 and 2, a system for creating a temperature gradient of at least 5° C. between a skin target and the surrounding skin, in accordance with the invention is shown. An applicator 703, to be described in detail below, contains a pair of RF electrodes 401 and 402 and a light source 403. The applicator 703 is adapted to be applied to the skin of an individual 705 in the region of a target. The applicator 703 is connected to a control unit 701 via a cable 702. The control unit 701 includes a power source 708. The power source 708 is connected to an RF generator 715 that is connected to the RF electrodes in the applicator 703 via wires in the cable 702. The power source 708 is also connected to a light source 403 in the applicator 703 via wires in the cable 702. The control unit 701 has an input device such as a keypad 710 that allows an operator to input selected values of parameters of the treatment, such as the frequency, pulse duration and intensity of the RF energy or the wavelength and intensity of the optical energy. The control unit 701 optionally contains a processor 709 for monitoring and controlling various functions of the device. For example, the processor 709 may monitor the electrical impedance between the electrodes in the applicator 703, and determine the temperature distribution in the vicinity of the target. The processor 709 may also determine the parameters of the treatment based upon the impedance measurements.

FIG. 2 shows the applicator 703 in detail. The applicator contains a pair of electrodes 401 and 402 that apply RF energy to the skin. A light source 403 produces a light spectrum that is delivered to the skin surface by light guide 404.

In accordance with the method of the invention, the system shown in FIG. 1 is used to first apply optical energy to a target having a diameter for example of 2 mm. A temperature gradient of 5° C. could be created if the optical energy has an intensity from about 5 to about 100 Joules/cm² and is applied from about 1 to 200 msec.

The parameters of RF energy may have the following exemplary values:

Frequency of the RF energy: from about 300 kHz to about 100 MHz.

Output power of the RF energy: from about 5 to about 200 W.

Duration of the irradiation: from about 1 to about 500 msec.

Pulse repetition rate: from about 0.1 to about 10 pulses per second.

Figure 3:
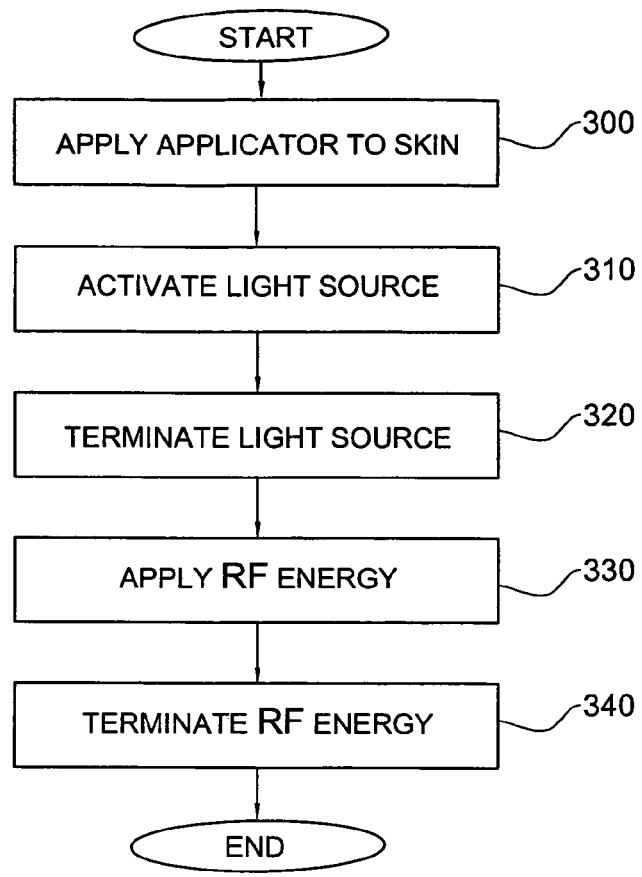
FIG. 3 shows an applicator with two electrodes, and a light source used in the system of FIG. 1.

FIG. 3 shows a flow chart for a method of treating skin using the system shown in FIGS. 1 and 2. In step 300, the applicator 703 is applied to the skin of an individual in the region of a target in the skin. In step 310 the light source 403 is activated so that the target is irradiated with optical energy from the light source 403 conducted through the optic fiber 404 to the target so as to heat the target to at least 5° C. above the temperature of the surrounding skin. In step 320 the irradiation with optical energy is terminated. RF energy is then applied to the skin (step 330). Finally, in step 340, the application of RF energy is terminated.

Figure 4:
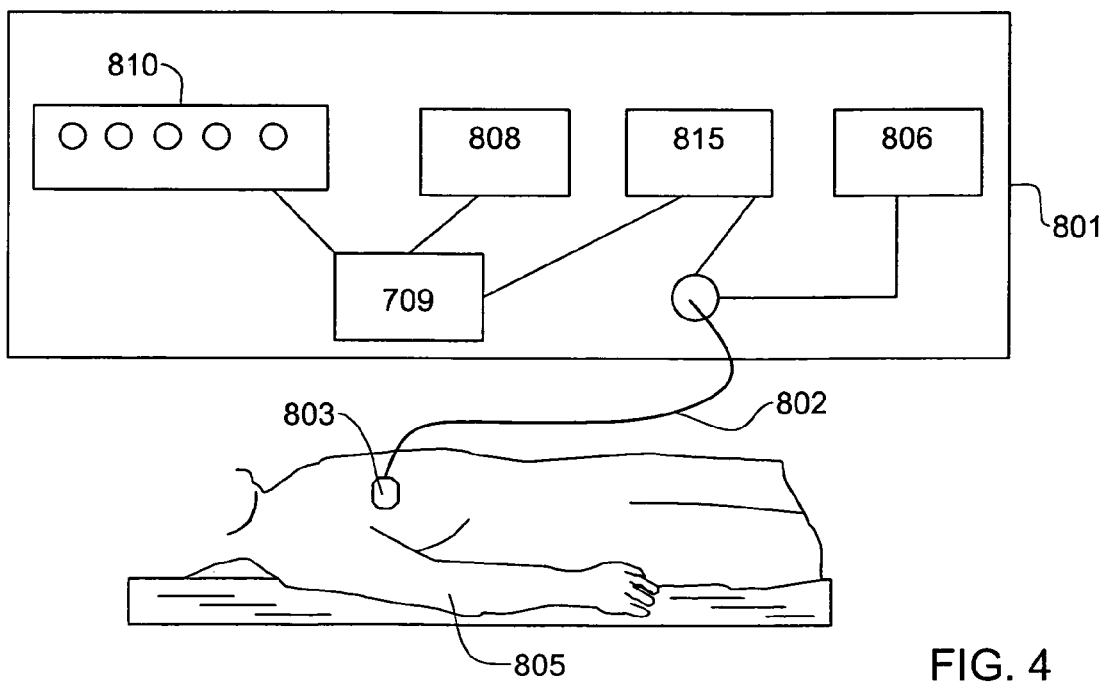
FIG. 4 shows a system for cooling skin surrounding a target and applying RF energy to an individual in accordance with another embodiment of the invention.
Figure 5:
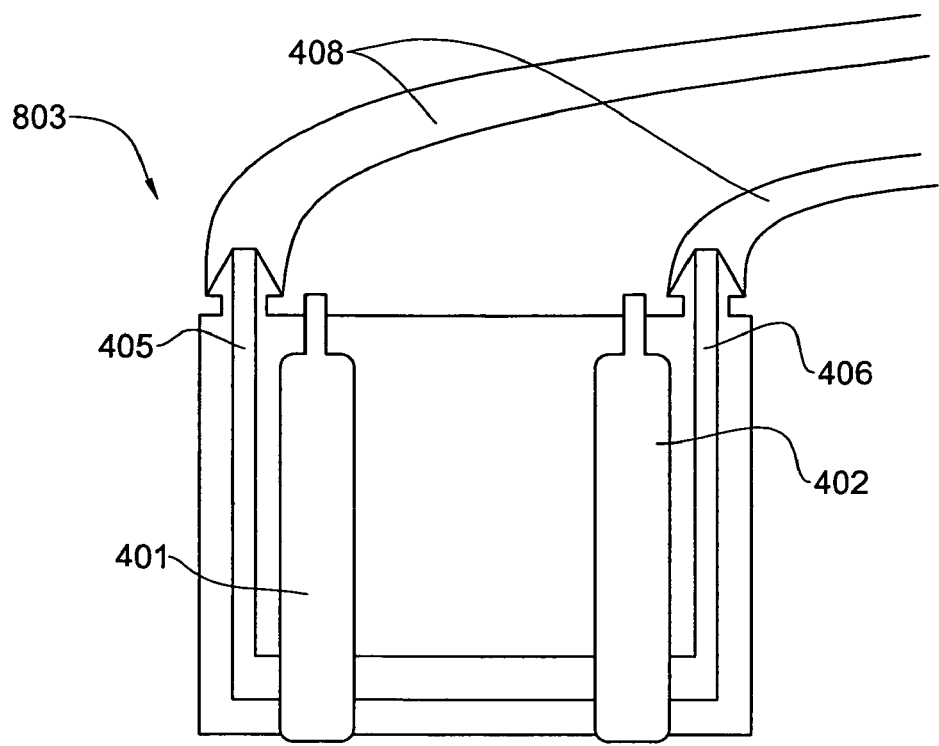
FIG. 5 shows an applicator with two electrodes, and a cooling system used in the system of FIG. 3.

Referring now to FIGS. 4 and 5, a system for creating a temperature gradient between a skin target and the surrounding skin, in accordance with another embodiment of the invention is shown. An applicator 803, to be described in detail below, contains a pair of RF electrodes 401 and 402. The applicator 803 is adapted to be applied to the skin of an individual 805 in the region of a target. The control unit 801 includes a power source 808. The power source 808 is connected to an RF generator 815 that is connected to the RF electrodes in the applicator 803 via wires in the cable 802. The control unit 801 controls a refrigeration unit 812 that cools a fluid such as ethanol or water for cooling the applicator 803. The cooled fluid flows from the refrigeration unit 812 to the applicator via a first tube in the cable 802, and flows from the applicator 803 back to the refrigeration unit via a second tube in the cable 802. The control unit 801 has an input device such as a keypad 810 that allows an operator to input selected values of parameters of the treatment, such as the frequency, pulse duration and intensity of the RF energy or the temperature of the coating fluid. The control unit 801 optionally contains a processor 809 for monitoring and controlling various functions of the device. For example, the processor 809 may monitor the electrical impedance between the electrodes in the applicator 803, and determine the temperature distribution in the vicinity of the target. The processor 809 may also determine the parameters of the treatment based upon the impedance measurements.

FIG. 5 shows the applicator 803 in detail. The applicator contains a pair of electrodes 401 and 402 that apply RF energy to the skin. The housing and electrodes are cooled by fluid cooled by the refrigeration unit 812 that flows in a tube 408 between inlet 405 and outlet 406. The inlet 405 and the outlet 406 are connected to the refrigeration unit 812 via the first and second tubes in the cable 802.

Figure 6:
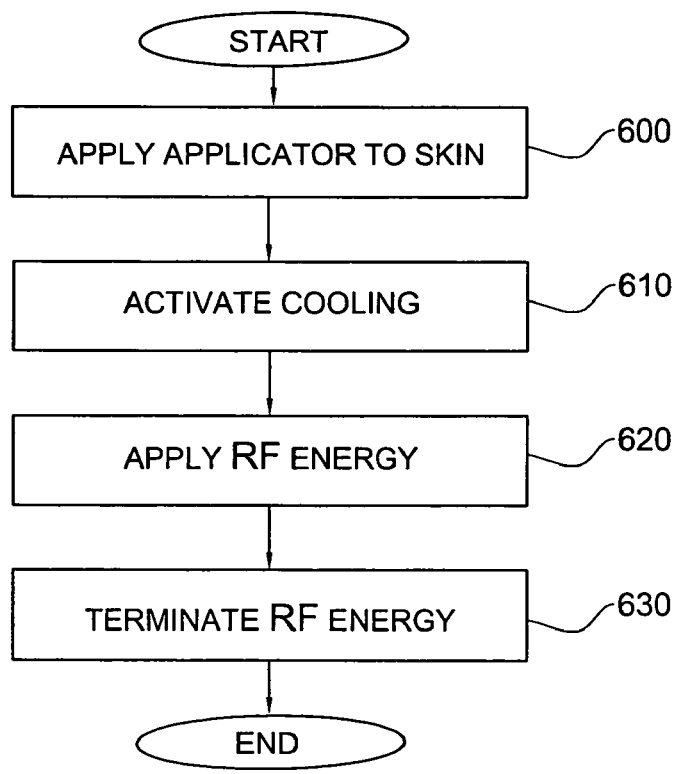
FIG. 6 shows a method for treating skin using the system of FIGS. 4 and 5.

FIG. 6 shows a flow chart for a method of treating skin using the system shown in FIGS. 4 and 5. In step 600, the applicator 703 is applied to the skin of an individual in the region of a target in the skin. In step 610 cooling system 812 is activated so that the skin surrounding the target is cooled to a temperature at least 5° C. below that of the target. RF energy is then applied to the skin (step 620). Finally, in step 630, the application of RF energy is terminated.

The invention claimed is:

1. A system for treating a skin surface target comprising:
   (a) an applicator containing at least two RF electrodes configured to be applied to the skin surface, so as to apply an RF current to a skin surface area located between the electrodes when the applicator is applied to the skin surface, the skin surface area containing at least a portion of the target;
   (b) a temperature effector configured to create a temperature difference between the target and a skin surface surrounding the target such that the target is at a temperature that is at least 5° C. higher than the surrounding skin surface, wherein the temperature effector heats the target.

2. The system according to claim 1 wherein the temperature effector comprises a light source configured to apply optical energy to the target.

3. A method for treating a skin surface target comprising:
   (a) creating a temperature gradient between the target and a skin surface surrounding the target such that the target is at a temperature that is at least 5° C. higher than the surrounding skin surface; and
   (b) applying RF energy to a skin surface area containing at least a portion of the target, wherein the temperature gradient is created by heating the target.

4. The method according to claim 3 wherein the target is heated by applying optical energy to the target with an intensity of about 5 to about 100 Joules/cm$^2$ for about 1 to 200 msec.

5. The method according to claim 3 wherein the target is selected from the group comprising a vascular lesion, pigmented lesion, hair follicle, wrinkle and acne.

6. The method of claim 3 wherein the RF energy has a power level of 5 to 200 W.

7. A method for treating a skin surface target comprising:
   (a) activating a temperature effector to heat the target in order to create a temperature gradient between the target and a skin surface surrounding the target such that the target is at a temperature that is at least 5° C. higher than the surrounding skin surface;
   (b) terminating the activity of the temperature effector; and
   (c) after said terminating step, applying RF energy to a skin surface area containing at least a portion of the target.

8. A system for treating a skin surface target comprising:
   an applicator containing at least two RF electrodes configured to be applied to the skin surface, so as to apply an RF current to a skin surface area located between the electrodes when the applicator is applied to the skin surface, the skin surface area containing at least a portion to the target;
   a temperature effector configured to heat the target in order to create a temperature difference between the target and skin surface surrounding the target such that the target is at a temperature that is at least 5° C. higher than the surrounding skin surface; and
   a processor coupled to said temperature effector and said RF electrodes and configured to sequentially activate said temperature effector, terminate the activity of said temperature effector, and then activate said RF electrodes.

* * * * *